United States Patent
Mulier et al.

[11] Patent Number: 6,063,081
[45] Date of Patent: *May 16, 2000

[54] FLUID-ASSISTED ELECTROCAUTERY DEVICE

[75] Inventors: Peter M. J. Mulier, St. Paul; Michael F. Hoey, Shoreview, both of Minn.

[73] Assignee: Medtronic, Inc., Minneapolis, Minn.

[ * ] Notice: This patent issued on a continued prosecution application filed under 37 CFR 1.53(d), and is subject to the twenty year patent term provisions of 35 U.S.C. 154(a)(2).

[21] Appl. No.: 08/393,082

[22] Filed: Feb. 22, 1995

[51] Int. Cl.⁷ .................................................. A61B 17/39
[52] U.S. Cl. .................................. 606/45; 606/49; 604/35
[58] Field of Search ................................ 606/41, 42, 45, 606/46, 48–50; 604/35

[56] References Cited

U.S. PATENT DOCUMENTS

| | | | |
|---|---|---|---|
| 4,307,720 | 12/1981 | Weber, Jr. | 128/276 |
| 4,506,680 | 3/1985 | Stokes | 128/786 |
| 4,641,649 | 2/1987 | Walinsky et al. | 128/303.1 |
| 4,674,498 | 6/1987 | Stasz | 128/303.14 |
| 4,682,596 | 7/1987 | Bales et al. | 128/303.14 |
| 4,748,979 | 6/1988 | Hershenson | 128/303.1 |
| 4,802,476 | 2/1989 | Norenberg et al. | 128/303.14 |
| 4,832,048 | 5/1989 | Cohen | 128/786 |

(List continued on next page.)

FOREIGN PATENT DOCUMENTS

| | | | |
|---|---|---|---|
| 0370890 | 5/1990 | European Pat. Off. | A61N 5/04 |
| 0499491 | 8/1992 | European Pat. Off. | A61N 1/05 |
| 0500215 | 8/1992 | European Pat. Off. | A61N 1/05 |
| 0500289 | 8/1992 | European Pat. Off. | A61N 1/05 |
| 2235669 | 1/1975 | France | 606/49 |
| 1007960 | 5/1957 | Germany | 606/49 |
| 9006079 | 6/1990 | WIPO | A61B 5/0402 |
| 9410924 | 5/1994 | WIPO | A61B 17/39 |
| 9410925 | 5/1994 | WIPO | A61B 17/39 |
| 9411059 | 5/1994 | WIPO | A61N 1/05 |

OTHER PUBLICATIONS

Reidenbach et al, "A New Method . . . Currents", Biomed Technik, 23 (1978), p. 71–74.

"Differential Response of Normal and Tumor Microcirculation to Hyperthermia," by T.E. Dudar et al, *Cancer Research,* vol. 44, Feb. 1984, pp. 605–612.

"Progress in Hyperthermia?," by J.R. Oleson, *Int. J. Radiation Oncology, Biology, Physics,* vol. 20, (Feb. 1991), p. 1143–1144.

"Percutaneous Transperineal Prostate Cryosurgery Using Transretal Ultrasound Guidance: Animal Model," by G. Onik et al., *Urology,* vol. 37, No. 3, (Mar. 1991) p. 277.

"Physical and Dynamic Characteristis of DC Ablation in Relation to the Type of Energy Delivery and Catheter Design," by Robert Lemery et al., *PACE,* vol. Jul. 1991, pp. 1158–1198.

"Basic and Clinical Studies of Local Hypothermia For Prostatic Cancer," by Masataka Hirai, *Nippon Hinyokika Gakkai Zasshi,* vol. 83, No. 5, May 1992, pp. 597–604.

"Interstitial Laser Hyperthermia," by A. Masters et al., *Seminars in Surgical Oncology,* vol. 8, (1992), pp. 242–249.

(List continued on next page.)

*Primary Examiner*—Lee S. Cohen
*Attorney, Agent, or Firm*—Harold R. Patton; Michael J. Jaro

[57] ABSTRACT

An electrocautery instrument is provided with a hollow electrode having a source of conductive fluid coupled to a proximal end thereof. Conductive fluid is communicated through said electrode and expelled out of the distal end thereof during electrocautery, forming a "virtual electrode." The infused conductive liquid conducts the RF electrocautery energy away from the conductive electrode, thereby displacing the region of thermal generation and reducing the extent of burns and perforations caused by conventional electrocautery electrodes. In one embodiment, the electrode is partially disposed within and extends distally out of a retractable suction tube, such that smoke and fluid are aspirated from the electrocautery site. When the suction tube is fully advanced, the electrode is concealed therein, enabling suction without electrocautery to be performed.

20 Claims, 1 Drawing Sheet

U.S. PATENT DOCUMENTS

| | | | |
|---|---|---|---|
| 4,850,353 | 7/1989 | Stasz et al. | 128/303.14 |
| 4,862,890 | 9/1989 | Stasz et al. | 128/303.14 |
| 4,869,248 | 9/1989 | Narula | 128/303.13 |
| 4,896,671 | 1/1990 | Cunningham et al. | 128/642 |
| 4,931,047 | 6/1990 | Broadwin et al. | 606/49 |
| 4,936,281 | 6/1990 | Stasz | 128/660.03 |
| 4,943,290 | 7/1990 | Rexroth et al. | 606/49 |
| 4,966,597 | 10/1990 | Cosman | 606/50 |
| 4,976,711 | 12/1990 | Parins et al. | 606/48 |
| 4,977,902 | 12/1990 | Sekino et al. | 128/804 |
| 4,979,948 | 12/1990 | Geddes et al. | 606/33 |
| 5,056,517 | 10/1991 | Fenici | 128/419 P |
| 5,057,107 | 10/1991 | Parins et al. | 606/48 |
| 5,078,717 | 1/1992 | Parins et al. | 606/48 |
| 5,083,565 | 1/1992 | Parins | 128/642 |
| 5,087,256 | 2/1992 | Taylor et al. | 606/28 |
| 5,098,431 | 3/1992 | Rydell | 606/48 |
| 5,122,137 | 6/1992 | Lennox | 606/40 |
| 5,125,928 | 6/1992 | Parins et al. | 606/48 |
| 5,129,396 | 7/1992 | Rosen et al. | 128/653.1 |
| 5,150,717 | 9/1992 | Rosen et al. | 128/804 |
| 5,167,659 | 12/1992 | Ohtomo et al. | 606/49 |
| 5,171,311 | 12/1992 | Rydell et al. | 606/48 |
| 5,178,618 | 1/1993 | Kandarpa | 606/28 |
| 5,188,635 | 2/1993 | Radtke | 606/14 |
| 5,192,280 | 3/1993 | Parins | 606/48 |
| 5,195,959 | 3/1993 | Smith | 606/42 |
| 5,197,963 | 3/1993 | Parins | 606/46 |
| 5,197,964 | 3/1993 | Parins | 606/48 |
| 5,215,103 | 6/1993 | Desai | 128/784 |
| 5,220,927 | 6/1993 | Astrahan et al. | 128/785 |
| 5,242,442 | 9/1993 | Hirschfeld | 606/42 |
| 5,269,781 | 12/1993 | Howell, III | 606/45 |
| 5,277,201 | 1/1994 | Stern | 607/98 |
| 5,281,217 | 1/1994 | Edwards et al. | 606/41 |
| 5,281,218 | 1/1994 | Imran | 606/41 |
| 5,290,286 | 3/1994 | Parins | 606/50 |

OTHER PUBLICATIONS

"Prediction of Treatment Temperatures in Clinical Hyperthermia of Locally Advanced Breast Carcinoma: The Use of Contrast Enhanced Computed Tomography," by H. Lyng et al., *Int. J. Radiation Oncology, Biol. Phys.*, vol. 26, (Jan. 1993), pp. 451–457.

"Thermometry of Interstitial Hyperthermia Given as an Adjuvant to Brachytherapy for the Treatment of Carcinoma of the Prostate," by S. D. Prionas et al., *Int. J. Radiation Oncology, Biol. Phys.*, vol. 28. (Sep. 1993), pp. 151–162.

"Transurethral Radio Frequency Thermomtherapy for Symptomatic Benign Prostatic Hyperplasia," by A. Corica et al., *Eur Urol*, vol. 23, 1993, pp. 313–317.

"Benign Prostatic Hypertrophy Treatment by Transurethral Radiofrequency Hyperthermia with Thermex II," by J.L. Viguier et al., *Eur Urol*, vol. 23, 1993, pp. 318–321.

"Transurethral Thermotherapy of the Benign Prostate Hypertrophy Controlled by Radiometry," by G. Belot et al., *Eur Urol*, vol. 23, 1993, pp. 326–329.

"Transurethral Needle Ablation (TUNA) of the Prostate Using Low–Level Radiofrequency Energy: An Animal Experimental Study," by B. Goldwasser et al., *Eur. Urol*, vol. 24, 1993, pp. 400–405.

"Needle Ablation Using Radio Frequency Current as a Treatment for Benign Prostatic Hyperplasia: Experimental Results in ex vivo Human Prostate," by J. Ramon et al., *Eur Urol*, vol. 24, 1993, pp. 406–410.

"Transurethral Needle Ablation (TUNA): Thermal Gradient Mapping and Comparison of Lesion Size in a Tissue Model and in Patients with Benign Prostatic Hyperplasia," by J.S. Rasor et al., *Eur Urol*, vol. 24, 1993, pp. 411–414.

"Transurethral Needle Ablation (TUNA): Safety Feasibility, and Tolerance of a New Office Procedure for Treatment of Benign Prostatic Hyperplasia," by C.C. Schulman et al., *Eur Urol*, vol. 24, 1993, pp. 415–423.

"Cooled Tip Ablation Results in Increased Radiofrequency Power Delivery and Lesion Size,"*PACE*, vol. 17, Apr. 1994, Part II, p. 782.

"Barriers to Drug Delivery in Solid Tumors," by R.K. Jain, *Scientific American*, vol. 271, No. 1, (Jul. 1994), pp. 58–65.

"Hyperthermia in Cancer Therapy: Where Are We Today and Where Are We Going?" by R. A. Steeves, *Bull. NY Acad. Med. (U.S.)* vol. 68, No. 2, Mar.–Apr., pp. 341–350.

Abstract 832, "Hydro–Ablation: A New Method for Trans–Catheter Radiofrequency Ablation," by S.W. Adler, et al., *Eur.J.C.P.E.*, vol. 4, No. 2, Jun. 1994.

Abstract 165, "Comparison of Radiofrequency (RF) Versus Microwave (MW) Energy Catheter Ablation of the Bovine Ventricular Mycardium," by L..A. Pires, M.D. et al., *PACE*, vol. 17, Apr. 1994, Part II.

Abstract 166, "Developing and Testing a Feedback Control System for Microwave Ablation: In Vitro and In Vivo Results," by P.J. Wang, M.D. et al, *PACE*, vol. 17, Apr. 1994, Part II.

Abstract 168, "Laser and Radiofrequency Catheter Ablation of Ventricular Myocardium in Dogs: a Comparative Test," by S. Enders, M.D. et al, *PACE*, vol. 17, Apr. 1994, Part II.

Abstract 0872, "Radiofrequency Delivery Through an Endocardial Cooled Catheter Results in Increased Lesion Size," by R. Ruffy et al, University of Utah, Salt Lake City, UT.

Abstract 0873, "Porous Metal Tipped Catheter Produces Larger Radiofrequency Lesions Through Tip Cooling," by D. Bergau et al, Children's Hospital, Boston, MA.

Abstract 287, "Comparison of Transesophageal Echocardiographic Guidance of Transseptal Left Heart Catheterization During Mitral Valvuloplasty and Radiofrequency Ablation of Left–Sided Accessory Pathways," by K.J. Tucker, M.D. et al, *PACE*, vol. 17, Apr. 1994, Part II.

Abstract 288, "Microwave Catheter Ablation via the Coronary Sinus: The Need for Power and Temperature Regulation?," by P.J. Wang, M.D. et al, *PACE*, vol. 17, Apr. 1994, Part II.

Abstract 290, "Electrode Temperature During Radiofrequency Catheter Ablation Procedures: Relationship to Ablation Target and Ablation Result," by H. Calkins, M.D. et al, *PACE*, vol. 17, Apr. 1994, Part II.

Abstract 485, "Comparison of Tissue Temperature and Lesion Size in Radiofrequency Ablation Using Saline Irrigation with a Small Versus Large Tip Electrode in a Canine Thigh Muscle Preparation," by H. Nakagawa, M.D. et al, *PACE*, vol. 17, Apr. 1994, Part II.

Abstract 487, "Intramural Ablation Using Radiofrequency Energy Via Screw–Tip Catheter and Saline Electrode," by M.F. Hoey MS, et al, *PACE*, vol. 17, Apr. 1994, Part II.

Abstract 1291, "Increase in the Lesion Size and Decrease in the Impedance Rise with a Saline Infusion Electrode Catheter for Radiofrequency Catheter Ablation," by S.K. Stephen Huang et al., *Circulation*, vol. 80, No. 4, Oct. 1989.

Abstract 121, "Tissue Temperatures in Radiofrequency Ablation Using a Saline Irrigated Electrode Versus Temperature Monitoring in a Canine Thigh Muscle Preparation," by H. Nakagawa et al., Abstracts from the 67th Scientific Sessions.

"Use of Saline Infusion Electrode Catheter for Improved Energy Delivery and Increased Lesion Size in Radiofrequency Catheter Ablation," by R.S. Mittleman et al., *PACE*, May 1995, Part I.

Abstract 705–5, "Comparison of Radiofrequency Lesions in the Canine Left Ventricle Using a Saline Irrigated Electrode Versus Temperature Control," by H. Nakagawa et al., *JACC*, Feb. 1995, p. 42A.

Abstract 777–1, "Effective Delivery of Radiofrequency Energy Through the Coronary Sinus without Impedance Rise Using a Saline Irrigated Electrode," by H. Nakagawa et al., *JACC*, Feb. 1995, p. 293A.

Abstract 22, "Tip Temperature is not an Indicator of Intramyocardial Temperatures During Radiofrequency Catheter Ablation," by Sean Mackey, MD, et al, *PACE*, vol. 17, Apr. 1994, Part II.

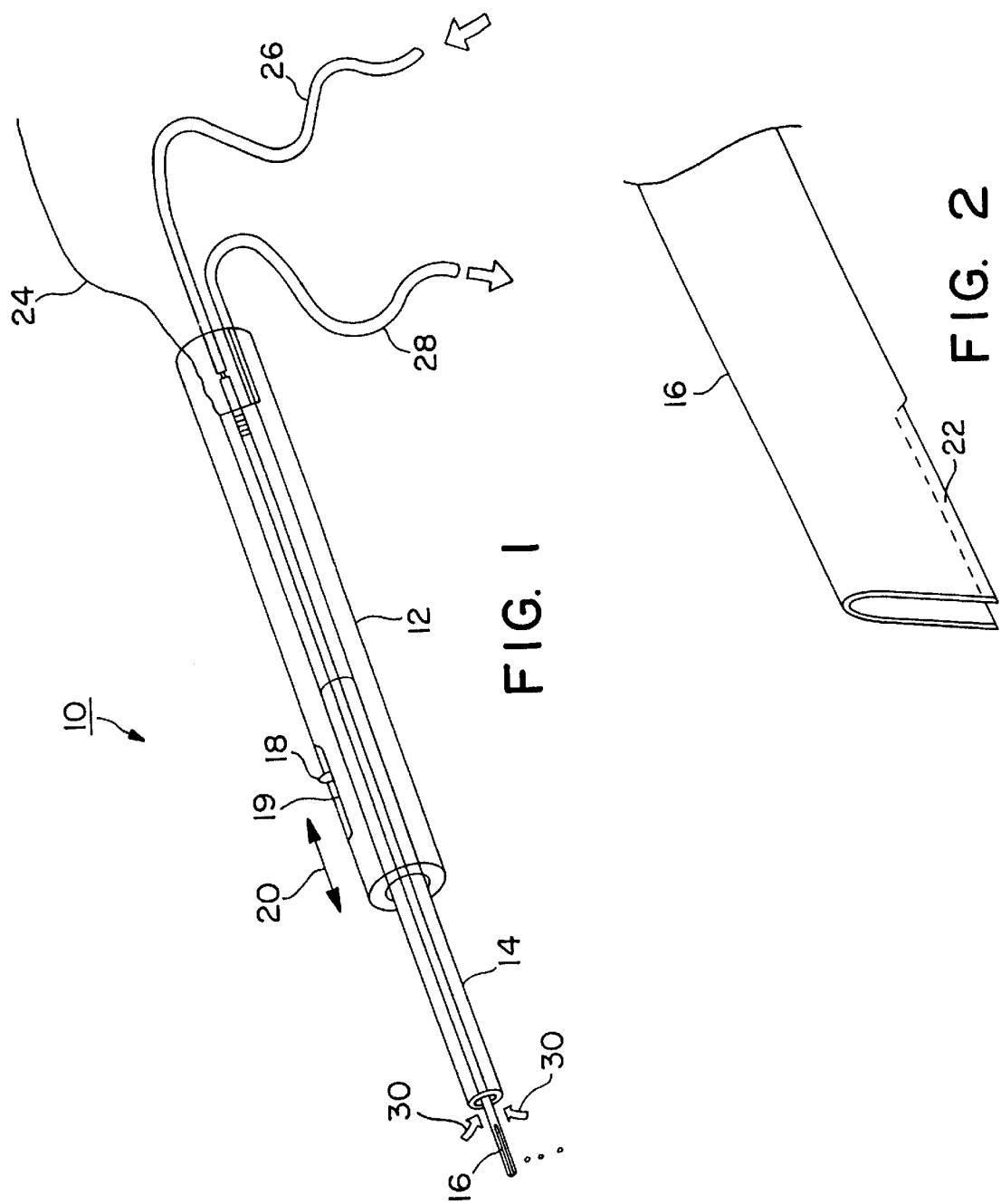

6,063,081

FLUID-ASSISTED ELECTROCAUTERY DEVICE

FIELD OF THE INVENTION

This invention relates generally to the field of medical instruments, and more particularly relates to an electrocautery device.

BACKGROUND OF THE INVENTION

Various types of electrocautery devices for incising and cauterizing body tissue are known and used in the medical field. Typically, such devices include a conductive blade or needle which serves as one electrode in an electrical circuit which is completed via a grounding electrode coupled to the patient. Incision of tissue is accomplished by applying a source of electrical energy (most commonly, a radio-frequency generator) to the blade. Upon application of the blade to the tissue, a voltage gradient is created, thereby inducing current flow and related heat generation at the point of contact. With sufficiently high levels of electrical energy, the heat generated is sufficient to cut the tissue and, advantageously, to simultaneously cauterize severed blood vessels.

It is widely recognized in the prior art that the often substantial amount of smoke produced by electrocauterization of tissue is at least unpleasant, and in some cases distracting or even hazardous to the operator and other attending medical personnel. As a result, it has been proposed, and is common, to provide an electrocautery device with smoke-aspirating capabilities, such that the smoke produced from electrocauterization is quickly withdrawn from the area of incision. Smoke aspiration may be accomplished by providing, in the handle of the electrocautery device near the electrocautery blade/electrode, an inlet port to be coupled to a vacuum or suction source. Examples of this are described in U.S. Pat. No. 4,307,720 to Weber, Jr., entitled "Electrocautery Apparatus and Method and Means for Cleaning the Same;" in U.S. Pat. No. 5,242,442 to Hirschfeld, entitled "Smoke Aspirating Electrosurgical Device;" and in U.S. Pat. No. 5,269,781 to Hewell, entitled "Suction Assisted Electrocautery Unit."

It has also been recognized in the prior art that the accumulation of coagulated blood, tissue rubble, and other debris on the electrode/blade of an electrocautery device can present a problem for the operator, necessitating the periodic cleaning of the blade, e.g., by wiping the blade over sterilized gauze or the like. This is generally regarded as undesirable, since the need to clean the electrode/blade tends to interrupt the incision procedure and increases the risks associated with contamination of the blade or the incision, damage to the blade, injury to the operator, and the like. To address this problem, it has been proposed in the prior art to provide an electrocautery instrument in which the electrode/blade is in slidable engagement with the instrument's handle, such that when the blade is retracted into the hand, any adhering debris automatically scraped off onto the tip of the handle. Such an instrument is proposed in the above-referenced Weber, Jr. '720 patent. While this arrangement may have some benefit, it still may be necessary to wipe off the tip of the handle once the blade is retracted. It is believed that a more direct and effective approach to the problem would be to reduce the amount of debris created during the electrocautery process, thereby eliminating or at least reducing the need to clean the electrode/blade.

SUMMARY OF THE INVENTION

In view of the foregoing considerations, the present invention is directed to an improved electrocautery instrument.

In one embodiment of the invention, an electrocautery instrument is configured with an electrode/blade disposed within a retractable suction tube, such that with the suction tube advanced, the electrode/blade is concealed within the tube, and with the suction tube retracted, the distal end of the electrode/blade is exposed for performing electrocautery.

In accordance with one aspect of the invention, the electrocautery electrode/blade is implemented with a hollow, conductive tube, flattened at it distal end into a blade-like configuration. Conductive fluid is applied to the proximal end of the hollow electrode/blade, and expelled from the distal (blade) end thereof during electrocautery. In accordance with another aspect of the invention, the conductive fluid emanating from the electrode/blade conducts the RF electrocautery energy away from the blade, so that it is primarily the fluid, rather than the metal blade, which actually accomplishes the cutting of tissue. That is, the fluid serves as a "virtual" electrocautery electrode. Since it is the fluid, rather than the blade, which incises and cauterizes, no burns or perforations are made to the tissue, reducing the amount of debris in the incision. Also, the flow of fluid through the electrode/blade tends to keep the blade clean and cool.

BRIEF DESCRIPTION OF THE DRAWINGS

The foregoing and other aspects of the present invention may perhaps be best appreciated with reference to a detailed description of a specific embodiment of the invention, when read in conjunction with the accompanying drawings, wherein:

FIG. 1 is a perspective view of an electrocautery instrument in accordance with one embodiment of the invention; and FIG. 2 is a enlarged perspective view of the distal end of the electrode/blade of the electrocautery instrument of FIG. 1.

DETAILED DESCRIPTION OF A SPECIFIC EMBODIMENT OF THE INVENTION

Referring to FIG. 1, there is shown a perspective view of a fluid-assisted electrocautery instrument 10 in accordance with one embodiment of the invention. Electrocautery instrument 10 comprises a handle 12, a suction tube 14, and an electrocautery electrode/blade 16. Handle 12 is preferably made of a sterilizable, rigid, and non-conductive material, such as nylon or the like. Suction tube 14, which is also preferably made of a sterilizable and non-conductive material, is slidably disposed partially within an internal lumen of handle 12, and projects distally out of the end thereof. Electrode/blade 16 is disposed within suction tube 14 and handle 12. Suction tube 18 is adapted to slide proximally and distally with respect to handle 12 and electrode 16 (i.e., in the directions of arrow 20 in FIG. 1) by means of a sliding lever 18 extending out of a slot 19 in handle 12. With suction tube 14 in a retracted position, as shown in FIG. 1, a distal portion of electrode/blade 16 projects beyond the distal end of tube 14, such that electrocautery can be performed. With suction tube in an advanced position, suction tube 14 completely conceals the tip of electrode/blade 16.

In accordance with one aspect of the invention, electrode/blade 16 is preferably implemented using a hollow cylindrical tube which has been flatted at its distal end, as shown in the greatly enlarged perspective view of FIG. 2. In addition to being flattened, a portion of the distal end of electrode/blade 16 is removed to form a longitudinal slit 22 therein.

Three connections are made to electrocautery instrument 10: One terminal (e.g., positive) of a radio-frequency (RF) generator (not shown in FIG. 1) is electrically coupled to electrode/blade 16 via a wire 24; a source of fluid to be expelled from slit 22 in electrode/blade 16 is coupled to the proximal end of electrode/blade 16 via a flexible tube or hose 26; and a suction hose 28 is coupled to handle 12 so as to be in communication with the internal lumen of handle 12 and with suction tube 14. When suction is applied via hose 28, air and fluid are drawn into the distal end of suction tube 14, as indicated by arrows 30. The ability to advance or retract suction tube 14 with respect to electrode/blade 16 enables the operator of the instrument to perform electrocautery while simultaneously aspirating smoke and fluid from the incision site, or to use suction tube 14 alone, without performing electrocautery.

As noted above, conductive fluid is communicated from inflow tube 26 and communicated along the length of electrode/blade 16 to be expelled from the distal end thereof. This is done in order to establish a so-called virtual electrode for performing electrocautery. The infusion of conductive fluid simultaneously with the application of RF energy is discussed in further detail in: U.S. patent application Ser. No. 08/113,441 entitled "Method and Apparatus for R-F Ablation," filed on Aug. 27, 1993 in the name of Peter M. J. Mulier and Michael F. Hoey, in U.S. patent application Ser. No. 08/303,246, entitled "Method and Apparatus for RF Ablation," filed on Sept. 8, 1994 in the name of Peter M. J. Mulier; and in U.S. patent application Ser. No. 08/302,304 entitled "Method and Apparatus for RF Ablation," filed in the name of Peter M. J. Mulier and Michael F. Hoey on Sept. 8, 1994. The foregoing '441 '246, and '304 applications (hereinafter collectively referred to as "the RF ablation applications") are each commonly assigned to the assignee of the present invention, and incorporated by reference herein in their respective entireties.

As described in the RF ablation patents, the infusion of conducting fluid into the area of application of RF energy creates a "virtual electrode," the size and shape of which can be controllably modified, and which can be rendered more or less conductive, thereby modifying the spread of RF energy. By varying such factors as the RF energy and duration, the rate of infusion of conductive liquid, and the conductivity of the infused solution, the size, shape, and intensity of the "virtual electrode"—i.e., the intensity of thermal production in the area, can be controlled. In the case of the electrocautery device in accordance with the present invention, application of the conductive solution during the application of RF energy further assists by preventing overheating of the electrode/blade, extending the point at which burning or charring of tissue would otherwise normally occur. To enhance this effect, it is contemplated that the solution being infused may first be cooled.

Conductive solutions believed to be suitable for establishing the virtual electrode include saline, saturated saline, and Ringer's solution, among others. Regarding the source of conductive fluid, it is contemplated that a conventional pump may be coupled to input line 26. Alternatively, it is contemplated that a small, pre-pressurized canister of conductive solution may be used, such that no pump is required. In one embodiment, handle 12 may be configured to receive such a pressurized canister therein, eliminating the need for input line 26.

Although in the embodiment of FIG. 1, input line 26, suction line 28, and electrical connection 24 are depicted separately, it is contemplated that these connections to instrument 10 may be consolidated into a single line having two separate fluid-conducting lumens therein (one for input of conductive solution, one for suction), alongside an insulated electrical conductor.

Various alternate configurations of electrode/blade 16 are also contemplated. In one embodiment, a porous metal element is substituted for the flattened tube configuration of FIGS. 1 and 2.

From the foregoing detailed description of a specific embodiment of the invention, it should be apparent that a method and apparatus for performing fluid-assisted electrocautery of body tissue has been disclosed, wherein fluid delivered out of a hollow electrocautery electrode/blade creates a virtual electrode which incises and cauterizes the tissue.

Although a specific embodiment of the invention has been described herein, this has been done solely for the purposes of illustrating various aspects of the invention, and is not intended to be limiting with respect to the scope of the invention. It is contemplated that various substitutions, alterations, and/or modifications, including but not limited to those specifically discussed herein, may be made to the disclosed embodiment without departing from the spirit and scope of the invention as defined in the appended claims, which follow.

We claim:

1. A fluid-assisted electrocautery instrument, comprising:
    an elongate handle having proximal and distal ends and having a longitudinal lumen extending between the proximal and distal ends;
    a suction tube, disposed partially within the lumen of the handle and having a distal end extending out of the distal end of the handle;
    a conductive electrocautery electrode adapted to be coupled to a source of radio-frequency energy, the electrode comprising an elongate tube defining an internal lumen extending between proximal and distal ends of the electrode, the electrode disposed within the suction tube such that a distal end of the electrode extends distally beyond the distal end of suction tube;
    a fluid input tube, coupled to the proximal end of the electrode and in fluid communication with the internal lumen of the electrode, such that conductive fluid supplied from the input tube flows along the electrode and is expelled from the distal end of the electrode.

2. An electrocautery instrument in accordance with claim 1, in which distal end of the electrode is flattened into a blade-like configuration.

3. An electrocautery instrument in accordance with claim 1, further comprising: a suction hose, coupled to a proximal end of the suction tube and adapted to be coupled to a suction pump, for aspirating smoke and fluid during electrocautery.

4. An electrocautery instrument in accordance with claim 1, in which the suction tube is slidably disposed in the handle such that the suction tube is slidable between a fully retracted position in which a distal end of the electrode extends beyond the distal end of the suction tube, and a fully advanced position in which the distal end of the electrode is disposed within the suction tube.

5. The electrocautery device of claim 2, in which a portion of the distal end of the electrode is removed to form a longitudinal slit.

6. A fluid-assisted electrocautery instrument, comprising:
    a handle having proximal and distal ends and having a lumen extending between the proximal and distal ends;
    a suction tube, located within the handle and having a proximal and a distal end, the suction tube capable of extending distally from the distal end of the handle;

a conductive electrocautery electrode having a proximal and a distal end, the electrode adapted to be coupled to a source of radio-frequency energy, the electrode comprising a tube defining an internal lumen extending between the proximal and distal ends of the electrode, the electrode extending distally beyond the distal end of the handle; and a fluid input tube, coupled to the proximal end of the electrode and in fluid communication with the internal lumen of the electrode, such that conductive fluid supplied from the input tube flows along the electrode and is expelled from the distal end of the electrode.

7. An electrocautery instrument in accordance with claim 6, in which the distal end of the electrode is flattened into a blade-like configuration.

8. An electrocautery instrument in accordance with claim 6 further comprising a suction hose, coupled to the proximal end of the suction tube and adapted to be coupled to a suction pump, for aspirating smoke and fluid through the distal end of the suction tube during electrocautery.

9. An electrocautery instrument in accordance with claim 6, wherein said suction tube is slidably disposed in said handle such that said suction tube is slidable between a fully retracted position wherein said distal end of said electrode extends beyond said distal end of said suction tube, and a fully advanced position wherein said distal end of said suction tube extends distally beyond said distal end of said electrode.

10. An electrocautery instrument in accordance with claim 6, wherein said electrode is disposed within said suction tube.

11. An electrocautery instrument in accordance with claim 10 in which the suction tube is movable relative to the electrode from a first position to a second position such that with the suction tube advanced, the electrode is concealed within the tube, and with the suction tube retracted, the distal end of the electrode is exposed for performing electrocautery.

12. A fluid-assisted electrocautery system, comprising:

a handle having proximal and distal ends and having a lumen extending between the proximal and distal ends;

a conductive electrocautery electrode disposed within the handle and having a proximal and a distal end, the electrode adapted to be coupled to a source of radio-frequency energy, the electrode comprising a tube defining an internal lumen extending between the proximal and distal ends of the electrode, the electrode extending distally beyond the distal end of the handle;

a fluid input tube, coupled to the proximal end of the electrode and in fluid communication with the internal lumen of the electrode, such that conductive fluid supplied from the input tube flows along the electrode and is expelled from the distal end of the electrode;

a radio-frequency (RF) generator electrically coupled to the electrode; and a suction tube within the handle and having a proximal and a distal end, the suction tube extending distally from the distal end of the handle.

13. The system of claim 12 further comprising a source of conductive fluid coupled to a proximal end of the fluid input tube.

14. The system of claim 12 further comprising a suction hose, coupled to the proximal end of the suction tube and adapted to be coupled to a suction pump, for aspirating smoke and fluid through the distal end of the suction tube during electrocautery.

15. The system of claim 14 wherein the suction tube is slidably disposed in the handle such that the suction tube is slidable between a fully retracted position in which the distal end of the electrode extends beyond the distal end of the suction tube, and a fully advanced position in which the distal end of the suction tube extends distally beyond the distal end of the electrode.

16. An apparatus for performing electrocautery, comprising:

means for applying radio-frequency energy to an electrocautery site via a hollow, conductive electrode comprising a conductive electrocautery electrode adapted to be coupled to a source of radio-frequency energy, the electrode comprising an elongate tube defining an internal lumen extending between proximal and distal ends of the electrode, the electrode disposed within a suction tube such that a distal end of the electrode extends distally beyond a distal end of the suction tube;

means for infusing the electrocautery site with a conductive liquid expelled from the electrode simultaneously with applying radio-frequency energy to the electrocautery site through the means for applying radio-frequency energy to an electrocautery site comprising a fluid input tube, coupled to the proximal end of the electrode and in fluid communication with the internal lumen of the electrode, such that conductive fluid supplied from the input tube flows along the electrode and is expelled from the distal end of the electrode.

17. A fluid-assisted electrocautery instrument, comprising:

an elongate handle having proximal and distal ends and having a longitudinal lumen extending between the proximal and distal ends;

a conductive electrocautery electrode adapted to be coupled to a source of radio-frequency energy, the electrode comprising an elongate tube defining an internal lumen extending between proximal and distal ends of the electrode, the electrode disposed within a suction tube such that a distal end of the electrode extends distally beyond a distal end of the suction tube;

a fluid input tube, coupled to the proximal end of the electrode and in fluid communication with the internal lumen of the electrode, such that conductive fluid supplied from the input tube flows along the electrode and is expelled from the distal end of the electrode.

18. An electrocautery instrument in accordance with claim 17, in which the distal end of the electrode is flattened into a blade-like configuration.

19. An electrocautery instrument in accordance with claim 18, further comprising a suction hose, coupled between to a proximal end of the suction tube and adapted to be coupled to a suction pump, for aspirating smoke and fluid during electrocautery.

20. An electrocautery instrument in accordance with claim 19, wherein in which the suction tube is slidably disposed in the handle such that the suction tube is slidable between a fully retracted position in which a distal end of the electrode extends beyond the distal end of the suction tube, and a fully advanced position in which the distal end of the electrode is disposed within the suction tube.

* * * * *

UNITED STATES PATENT AND TRADEMARK OFFICE
CERTIFICATE OF CORRECTION

PATENT NO. : 6,063,081
DATED : May 16, 2000
INVENTOR(S) : Peter M. J. Mulier and Michael F. Hoey It is certified that error appears in the above-identified patent and that said Letters Patent is hereby corrected as shown below:

Column 6,
Line 53, "with claim 18:" should read -- with claim 17: --
Line 58, "with claim 19:" should read -- with claim 17: --

Signed and Sealed this

Eighth Day of April, 2003

JAMES E. ROGAN
*Director of the United States Patent and Trademark Office*